US00PP30069P2

(12) United States Plant Patent
Eveleens

(10) Patent No.: US PP30,069 P2
(45) Date of Patent: Jan. 8, 2019

(54) ***HYDRANGEA* PLANT NAMED 'HORTMASUN'**

(50) Latin Name: *Hydrangea macrophylla*
Varietal Denomination: Hortmasun

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING B.V., Aalsmeer (NL), part interest; KOLSTER HOLDING B.V., Boskoop (NL), part interest ( * ) Notice: Subject to any disclaimer, the term of this patent is extended or adjusted under 35 U.S.C. 154(b) by 0 days.

(21) Appl. No.: 15/731,900

(22) Filed: Aug. 21, 2017

(51) Int. Cl.
*A01H 5/00* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Hortmasun' that is characterized by its mophead type inflorescences with sterile flower sepals that are pink in color with white margins, its sterile flower sepals with a sturdy and thick texture and its strong rooting habit.

2 Drawing Sheets

Botanical classification: *Hydrangea macrophylla.*
Varietal denomination: 'Hortmasun'.

BACKGROUND OF THE INVENTION

The present invention relates to a new and distinct cultivar of *Hydrangea macrophylla* and will be referred to hereafter by its cultivar name, 'Hortmasun'. 'Hortmasun' represents a new big leaf *hydrangea*, a perennial shrub grown for landscape use.

'Hortmasun' was derived from an ongoing controlled breeding program directed by the Inventor in Boskoop, The Netherlands. The objective of the breeding program was to develop new cultivars of *Hydrangea* with bi-colored sterile flowers that are pink with white margins and that exhibit strong rooting. 'Hortmasun' arose from a controlled cross made by the Inventor in April of 2006 between unnamed and unpatented proprietary plants in the Inventor's breeding program; reference no. 03-015-06 as the female parent and reference no. 02-029-06 as the male parent. 'Hortmasun' was selected as a single unique plant from amongst the resulting seedlings in August of 2015.

Asexual propagation of the new cultivar was first accomplished by stem cuttings by the Inventor in Boskoop, The Netherlands in August of 2008. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hortmasun' as a unique cultivar of *Hydrangea macrophylla.*

1. 'Hortmasun' exhibits mophead type inflorescences with sterile flower sepals that are pink in color with white margins.

2. 'Hortmasun' exhibits sterile flower sepals with a sturdy and thick texture.
3. 'Hortmasun' exhibits a strong rooting habit.

The female parent of 'Hortmasun' differs from 'Hortmasun' in having sterile flower sepals that are solid pink and darker pink in color. The male parent of 'Hortmasun' differs from 'Hortmasun' in having a less vigorous growth habit due to having a weaker rooting habit, and being less floriferous by producing less flowering stems. 'Hortmasun' can be most closely compared to the *Hydrangea macrophylla* cultivars 'Harlequin' (not patented) and 'Hortmaserena' (not patented). Both cultivars are similar to 'Hortmasun' in having bicolored sterile flowers. 'Harlequin' differs from 'Hortmasun' in having flowering stems that are longer and less sturdy, less branching and sterile flower sepals that are softer in texture. 'Hortmaserena' differs from 'Hortmasun' in having sterile flower sepal that are much darker pink in color with thinner white margins and flowering stems that are longer.

BRIEF DESCRIPTION OF THE DRAWINGS

The accompanying colored photographs illustrate the overall appearance and distinct characteristics of the new *Hydrangea.* The photographs were taken of a plant two years in age as grown in a 17-cm container in a greenhouse in Boskoop, The Netherlands.

The photograph in FIG. 1 provides a side view of the plant habit of 'Hortmasun' in bloom.

Figure 1:
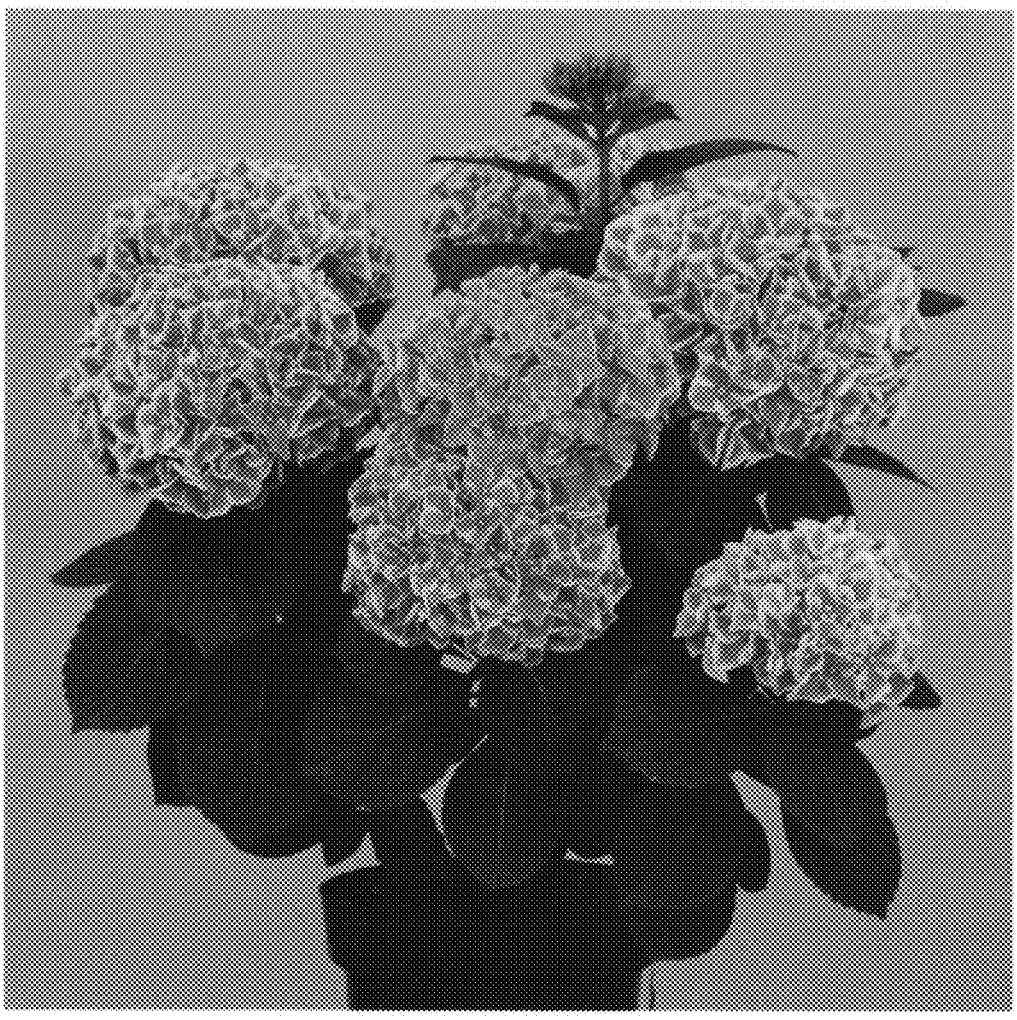
Figure 2:
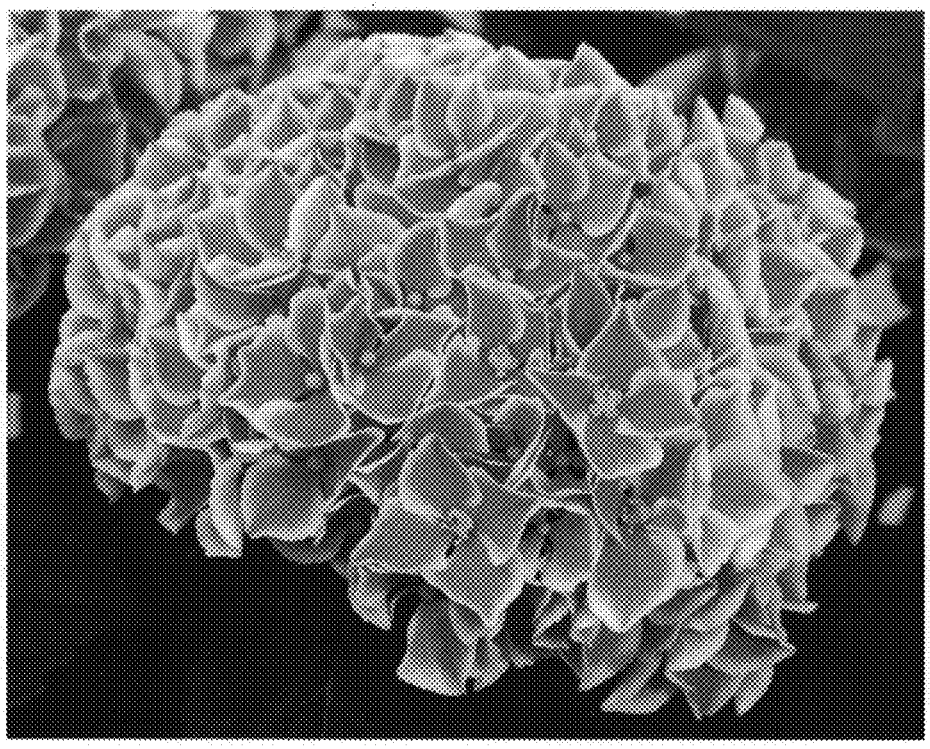

The photograph in FIG. 2 provides a close-up view of an inflorescence of the inflorescences of 'Hortmasun'.

Figure 3:
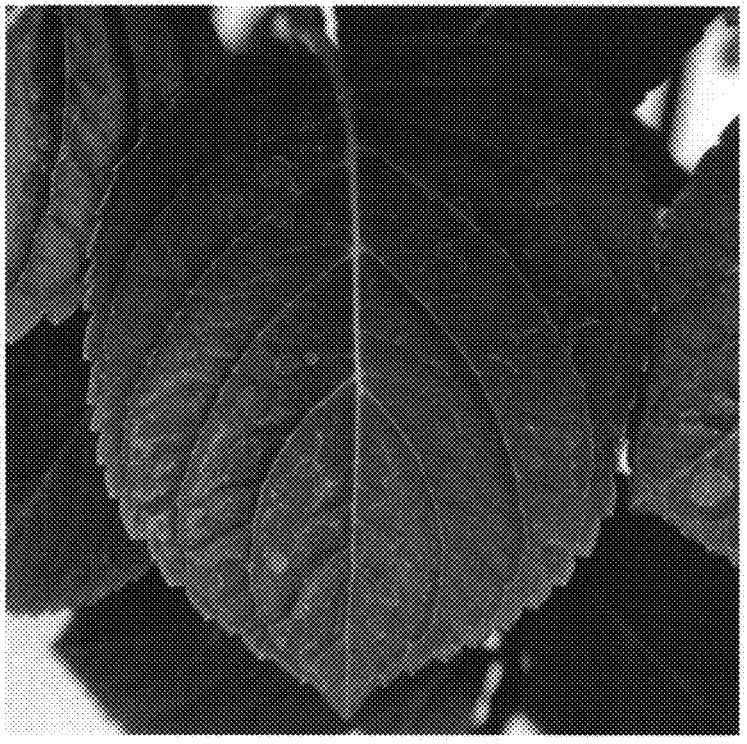

The photograph in FIG. 3 provides a close-up view of a leaf of 'Hortmasun'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants two years in age as grown in 17-cm containers in a greenhouse in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Two months in summer in The Netherlands.

*Plant type.*—Perennial shrub, mophead type *hydrangea.*

*Plant habit.*—Broadly spreading to upright.

*Height and spread.*—An average of 46.8 cm in height and 46.8 cm in spread as grown in a 17-cm container and an average of 1 m in height and width as a 3 year-ld plant in the landscape.

*Hardiness.*—At least in U.S.D.A. Zones 5 to 9.

*Diseases and pests.*—No susceptibility or resistance to pests and diseases has been observed.

*Root description.*—Fibrous and fine, 199D in color.

*Propagation.*—Stem cuttings.

*Time required for root development.*—An average of 3.5 weeks for root initiation with a young rooted plant produced in an average of six months.

*Growth rate.*—Moderate.

Stem description:

*Stem shape.*—Rounded.

*Stem strength.*—Strong.

*Stem aspect.*—Upright to an average angle of 60° to soil.

*Stem color.*—Immature stems; 143A to 143B, mature stems; 144A, older bark; N199A to N199B.

*Stem size.*—An average of 23 cm (excluding the inflorescence) in length and 6.5 mm in diameter.

*Stem surface.*—Immature and mature stems; glabrous and moderately lenticellate with lenticels; an average of 1 mm in length and 0.5 mm in width, and too small to measure color.

*Branching.*—Moderately branched with an average of 10 lateral branches, branching improves with pinching.

*Internode length.*—An average of 4.1 cm.

Foliage description:

*Leaf shape.*—Broad ovate to near oblong.

*Leaf arrangement.*—Opposite.

*Leaf division.*—Simple.

*Leaf number.*—An average of 10 (5 pairs) per lateral branch.

*Leaf base.*—Obtuse to short attenuate.

*Leaf apex.*—Bluntly apiculate.

*Leaf margins.*—Serrate.

*Leaf venation.*—Pinnate, color; upper surface 144A to 144B, lower surface 144B, lower surface main and lateral veins are covered with short hairs; an average of 0.2 mm in length and too small to measure color.

*Leaf size.*—An average of 12.1 cm in length and 9.7 cm in width.

*Leaf attachment.*—Petiolate.

*Leaf surface.*—Upper surface smooth to slightly rugose, lower surface smooth and very slightly rugose.

*Leaf color.*—Young leaves upper surface NN137A, young leaves lower surface 146A to 147B, mature leaves upper surface between NN137A and 147A, mature leaves lower surface 147B.

*Petioles.*—An average of 1.5 cm in length and 3.5 mm in diameter, color; upper surface 144A to 144B, lower surface 144A, surface smooth and dull, strong.

Inflorescence description:

*Inflorescence type.*—Flattened globular, mophead type, compound corymb of rotate-shaped sterile flowers over fertile flowers.

*Lastingness of inflorescence.*—Sterile flowers; an average of 6 weeks, persistent, fertile flowers; an average of 1 week, self-cleaning.

*Inflorescence number.*—One per lateral stem.

*Inflorescence size.*—An average of 11.1 cm in height and 17.5 cm in diameter.

*Flower number.*—An average of 250 sterile flowers and 100 fertile flowers per inflorescence.

*Flower fragrance.*—None.

*Flower aspect.*—Sterile flowers; upright, outwards, and slightly drooping, fertile flowers; upright.

*Flower size.*—Sterile flowers; an average of 3.6 cm in diameter and 1.3 cm in depth, fertile flowers; an average of 1 cm in diameter and 6 mm in depth.

*Flower shape.*—Sterile and fertile flowers; rotate.

*Flower buds.*—Sterile flowers; an average of 2 mm in length and 3 mm in diameter, globular in shape, color; 73D, fertile flowers; an average of 3 mm in length and diameter, obovate in shape, color; 68D with base 150C.

*Peduncles.*—An average of 10 cm in length and 8 mm in diameter, held upright to outwards, 144A in color, smooth surface, strong.

*Pedicels.*—Sterile flowers; an average of 2 cm in length and 1.5 mm in diameter, held at an average angle of 40° to peduncle, 70C in color, moderate strength, dull surface is moderately covered with thin hairs; an average of 0.2 mm in length and too small to measure color, fertile flowers; an average of 3 mm in length and 1 mm in diameter, held at an average angle of 10° to vertical, 62A in color, moderate strength, dull and glabrous surface.

*Petals.*—Sterile flowers; 4, occasionally 5, rotate (cruciform in 4-petalled flowers), ovate in shape, concave, acute apex, cuneate base, entire margin, an average of 4 mm in length and 2 mm in width, glabrous and dull upper and lower surfaces, color when opening and when fully open upper and lower surface 68C, fertile flowers; an average of 4, occasionally 5, rotate (cruciform in 4-petalled flowers), ovate in shape, concave, acute apex, cuneate base, entire margin, an average of 5 mm in length and 2.5 mm in width, color; upper and lower surface when opening 75C, upper and lower surface when fully open 75C, fading to 155A at the margins and base, both surfaces glabrous and dull.

*Sepals.*—Sterile flowers; 4, occasionally 5, rotate (cruciform in 4-petalled flowers), broadly rhomboidal to broad obovate in shape, apex; bluntly short apiculate, cuneate base, margin; entire to slightly irregularly dentate to serrate, an average of 2.2 cm in length and 2.3 cm in width, color; upper surface when opening 63B with margins 62D, lower surface when opening 63C with margins 62D, upper surface when fully open 63B with margins NN155C, lower surface when fully open 64D with margins NN155B, both surfaces; glabrous and dull, fertile flowers; an average of 6, occasionally 5, rotate in arrangement, deltoid in shape, acute apex, broadly cuneate base, entire margin, an average of 1 mm in length and width, color; upper and lower surface when opening and when fully open 150D and strongly flushed with 67D, both surfaces glabrous and dull.

Reproductive organs:

*Gynoecium.*—Sterile flowers; 3 pistils, an average of 1 mm in length, stigma; club-shaped and NN155C in color, style; 0.6 mm in length, 65D in color, ovary is 157D in color, fertile flowers; an average of 3 to 4 pistils; an average of 1 mm in length, stigma; club-shaped and N155C in color, style; 0.6 mm in length, 65D in color, ovary is 150C to 150D in color.

*Androecium.*—Sterile flowers; an average of 8 stamens, filaments; an average of 2.5 mm in length and N155D in color, anthers; oblong in shape, an average of 1 mm in length and 76C in color, pollen is moderate in quantity and 159D in color, fertile flowers; an average of 10 stamens, filaments; an average of 2.5 mm in length and N155D in color, anthers; oblong in shape, an average of 1 mm in length and 76C in color, pollen is moderate in quantity and 159D in color.

*Fruit and seed.*—No seeds or fruit observed to date.

It is claimed:

1. A new and distinct cultivar of *Hydrangea* plant named 'Hortmasun' substantially as herein illustrated and described.

* * * * *